(12) United States Patent
Sase

(10) Patent No.: US 10,527,838 B2
(45) Date of Patent: **\*Jan. 7, 2020**

(54) ANALYSIS DEVICE, MICROSCOPE DEVICE, ANALYSIS METHOD, AND PROGRAM

(71) Applicant: NIKON CORPORATION, Tokyo (JP)

(72) Inventor: Ichiro Sase, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,827

(22) Filed: Jan. 4, 2019

(65) Prior Publication Data

US 2019/0137754 A1 May 9, 2019

Related U.S. Application Data

(63) Continuation of application No. 15/079,568, filed on Mar. 24, 2016, now Pat. No. 10,268,033, which is a (Continued)

(30) Foreign Application Priority Data

Sep. 27, 2013 (JP) .................. 2013-200705

(51) Int. Cl.
  *G02B 21/36* (2006.01)
  *G02B 21/16* (2006.01)
  (Continued)

(52) U.S. Cl.
  CPC ....... *G02B 21/367* (2013.01); *G01N 21/6458* (2013.01); *G02B 21/16* (2013.01);
  (Continued)

(58) Field of Classification Search
  CPC ...... G02B 21/367; G02B 21/16; G02B 27/56; G02B 27/58; G06T 7/90; G06T 7/11;
  (Continued)

(56) References Cited

U.S. PATENT DOCUMENTS

| 8,988,771 B2 | 3/2015 | Kleppe et al. |
| 2003/0170613 A1 | 9/2003 | Straus |

(Continued)

FOREIGN PATENT DOCUMENTS

| DE | 102009031231 A1 | 12/2010 |
| DE | 102010035003 A1 | 2/2012 |

(Continued)

OTHER PUBLICATIONS

Sara A Jones et al; "Fast three-dimensional super-resolution imaging of live cells"; Nature Methods, Advance Online Publication, 2011 Nature America Inc.; pp. 1-10.

(Continued)

*Primary Examiner* — Ali Bayat
(74) *Attorney, Agent, or Firm* — Oliff PLC

(57) ABSTRACT

An analysis device for quantifying a state of a fluorescent image containing a plurality of bright spots comprises an area setting unit in which states of a plurality of bright spots contained in a plurality of areas set in the fluorescent image in accordance with positions of the plurality of bright spots are quantified as numerical values.

10 Claims, 12 Drawing Sheets

Related U.S. Application Data continuation of application No. PCT/JP2014/075658, filed on Sep. 26, 2014.

(51) Int. Cl.

| | | |
|---|---|---|
| *G02B 27/56* | (2006.01) | |
| *G02B 27/58* | (2006.01) | |
| *G01N 21/64* | (2006.01) | |
| *G06T 7/11* | (2017.01) | |
| *G06T 7/90* | (2017.01) | |

(52) U.S. Cl.
CPC .............. *G02B 27/56* (2013.01); *G02B 27/58* (2013.01); *G06T 7/11* (2017.01); *G06T 7/90* (2017.01); *G06T 2207/10056* (2013.01); *G06T 2207/10064* (2013.01); *G06T 2207/20021* (2013.01)

(58) Field of Classification Search
CPC ......... G06T 7/0012; G06T 2207/10024; G06T 2207/10056; G06T 2207/10064; G06T 2207/20021; G06T 2207/20092; G06T 2207/30024; G06K 9/0014; G06K 9/6253; G06K 2009/366; G01N 21/16
USPC ........................................................ 382/164
See application file for complete search history.

(56) References Cited

U.S. PATENT DOCUMENTS

| | | | |
|---|---|---|---|
| 2006/0040400 A1 | 2/2006 | Mizutani et al. | |
| 2007/0146869 A1 | 6/2007 | Lauer | |
| 2008/0032414 A1 | 2/2008 | Zhuang et al. | |
| 2010/0053211 A1* | 3/2010 | Ingermanson | G06K 9/0014 345/626 |
| 2010/0061617 A1* | 3/2010 | Ingermanson | G06K 9/0014 382/133 |
| 2011/0002530 A1 | 1/2011 | Zhuang et al. | |
| 2011/0226965 A1 | 9/2011 | Wolleschensky et al. | |
| 2011/0321204 A1 | 12/2011 | Karaki et al. | |
| 2012/0140317 A1* | 6/2012 | Kleppe | G01N 21/6458 359/385 |
| 2012/0231489 A1 | 9/2012 | Lenhert | |
| 2012/0288157 A1* | 11/2012 | Kishima | G06T 7/571 382/106 |
| 2012/0305803 A1 | 12/2012 | Foelling | |
| 2013/0022268 A1* | 1/2013 | Kishima | G06T 5/002 382/173 |
| 2013/0057873 A1 | 3/2013 | Brown, III et al. | |
| 2015/0192767 A1 | 7/2015 | Li et al. | |
| 2016/0202465 A1 | 7/2016 | Sase | |

FOREIGN PATENT DOCUMENTS

| | | |
|---|---|---|
| EP | 3051276 A1 | 8/2016 |
| JP | 2011-508214 A | 3/2011 |
| JP | 2012-510066 A | 4/2012 |
| JP | 2012-530947 A | 12/2012 |
| JP | 2013-015325 A | 1/2013 |
| JP | 2013-015665 A | 1/2013 |
| WO | 2009/085218 A1 | 7/2009 |
| WO | 2011/098304 A1 | 8/2011 |
| WO | 2015/046440 A1 | 4/2015 |

OTHER PUBLICATIONS

Dec. 22, 2014 Search Report issued in International Patent Application No. PCT/JP2014/075658.
Dec. 22, 2014 Written Opinion issued in International Patent Application No. PCT/JP2014/075658.
Nov. 22, 2016 Office Action issued in Japanese Patent Application No. 2015-539385.
Jun. 27, 2017 Office Action issued in U.S. Appl. No. 15/079,568.
Stefan Geissbuehler et al, "Comparison between SOFI and STORM", Biomedical Optics Express, vol. 2, No. 3, p. 408, Mar. 1, 2011.
Apr. 25, 2017 Office Action issued in Japanese Patent Application No. 2015-539385.
Apr. 28, 2017 Search Report issued in European Patent Application No. 14850023.4.
Apr. 24, 2018 Office Action issued in U.S. Appl. No. 15/079,568.
Jan. 8, 2019 Office Action issued in Japanese Patent Application No. 2018-025052.
Oct. 2, 2018 Notice of Allowance issued in U.S. Appl. No. 15/079,568.

\* cited by examiner

ANALYSIS DEVICE, MICROSCOPE DEVICE, ANALYSIS METHOD, AND PROGRAM This is a Continuation Application of U.S. patent application Ser. No. 15/079,568 filed on Mar. 24, 2016 which is a Continuation Application of International Application No. PCT/JP2014/075658, filed on Sep. 26, 2014, which claims priority to Japanese Patent Application No. 2013-200705, filed on Sep. 27, 2013, the contents of the above applications being hereby incorporated by reference.

BACKGROUND

Technical Field

The present invention relates to an analysis device, a microscope device, an analysis method, and a program.

The present application claims priority to Japanese Patent Application No. 2013-200705, filed Sep. 27, 2013, the content of which is incorporated herein by reference.

Background Art

Super-resolution microscopes are microscope devices which use fluorescence techniques to allow for observation beyond the resolution of an optical system. One embodiment of known super-resolution microscopy is stochastic optical reconstruction microscopy (STORM; e.g. see Patent Document 1). In STORM, a fluorescent material or object with said fluorescent material adhered thereto is used as an observation sample. This fluorescent material has properties whereby it becomes active when irradiated with activation light of a predetermined wavelength and, thereafter, becomes inactive by emitting fluorescence when irradiated with excitation light of a wavelength different from the activation light. A fluorescent image is acquired by irradiating the observation sample with activation light at a low power so as to activate the fluorescent material at a low density and then applying excitation light so as to cause the fluorescent material to emit light. In a fluorescent image acquired in this manner, fluorescent bright spots (images of the fluorescent material) are distributed at low density and are individually isolated. As a result, the center-of-gravity position of each individual image can be determined. This step of acquiring a fluorescent image is repeated multiple times, e.g. hundreds to tens of thousands of times, and the resulting fluorescent images are synthesized through image processing to enable the generation of a sample picture image of high resolution.

In STORM, a technique for determining the locations of the fluorescent bright spots is known in which the locations of the fluorescent bright spots are pseudo-calculated from the results of calculating the probability distribution based on obtained data (Gaussian distribution) (e.g. see Non-Patent Document 1).

CITATION LIST

Patent Literature

Patent Document 1: U.S. Patent Application Publication No. 2008/0032414

Non Patent Literature

Non-Patent Document 1: Sara A Jones, Sang-Hee Shim, Jiang He & Xiaowei Zhuang, "Fast, three-dimensional super-resolution imaging of live cells", Nature America, Inc., 2011

SUMMARY

Technical Problem

However, while it is possible to acquire fluorescent images at high resolution using STORM, the bright spot data (e.g. number of photons, ellipticity, etc.) are localized to particular coordinates (e.g. center-of-gravity position, etc.). As a result, there is a problem in that quantitative analysis such as that including basic arithmetic operations using the pixel intensity value (quantity of fluorescent light) of the image (or between images) cannot be performed.

An object of the aspects according to the present invention is to provide an analysis device capable of performing quantitative analysis based on images of high resolution, a microscope device, an analysis method, and a program.

Solution to Problem

An analysis device according to an aspect of the present invention is an analysis device for quantifying a state of a fluorescent image containing a plurality of bright spots. The analysis device comprises an area setting unit in which states of the plurality of bright spots contained in a plurality of areas set in the fluorescent image in accordance with positions of the plurality of bright spots are quantified as numerical values.

A microscope device according to an aspect of the present invention comprises a sample picture image generating device that generates a fluorescent image containing the plurality of bright spots by displaying the positions of the images of a fluorescent material contained in the acquired fluorescent image as bright spots.

An analysis method of an aspect according to the present invention is an analysis method for quantifying a state of a fluorescent image containing a plurality of bright spots. The analysis method comprises an area setting process in which states of the bright spots contained in a plurality of areas set in the fluorescent image in accordance with positions of the plurality of bright spots are quantified as numerical values.

An aspect according to the present invention is a program for allowing a computer of an analysis device for quantifying a state of a fluorescent image containing a plurality of bright spots to execute an area setting step in which states of bright spots contained in a plurality of areas set in the fluorescent image in accordance with positions of the plurality of bright spots are quantified as numerical values.

An analysis device of an aspect according to the present invention is an analysis device for quantifying a state of a fluorescent image containing a plurality of bright spots. The analysis device comprises an area setting unit in which states of the bright spots contained in each area of a plurality of preset areas set in the fluorescent image are quantified as numerical values.

Advantageous Effects of Invention

According to the aspects of the present invention, quantitative analysis based on images of high resolution can be performed.

DESCRIPTION OF EMBODIMENTS

Figure 1:
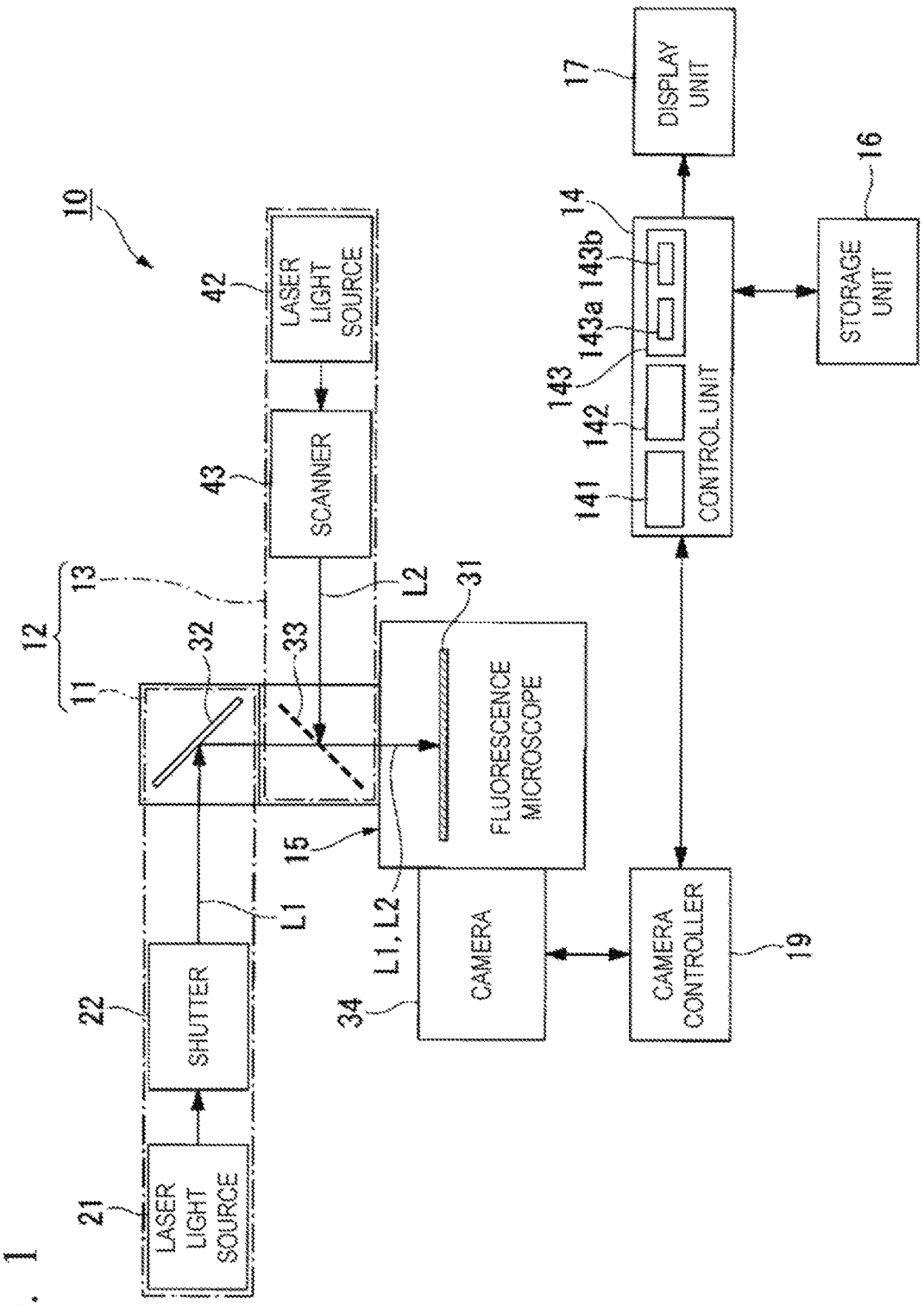
FIG. 1 is a configuration diagram illustrating a first embodiment of a microscope device.

Hereinafter, an embodiment of a microscope device and an image generation method will be described while referring to the drawings.

First, a summary will be presented of an analysis method for quantitatively analyzing a subject having movement similar to that of a living cell.

For example, analysis techniques exist for quantitatively analyzing the state of a cell from fluorescent images that have been observed continuously. In conventional analysis techniques, acquired fluorescent images are used with a pixel of an optical receiving element being treated as the smallest unit of space. Thus, the intensity distribution data of the fluorescent image (intensity distribution and the like of fluorescent light emitted from the fluorescent material contained in the observation sample) is allocated at the "pixel" smallest unit of space, and basic arithmetic operations using intensity values (fluorescent light quantity) of the pixels (or between the pixels), or, in other words, basic arithmetic operations using the pixel intensity values of the images (or between the images) can be quantitatively performed. Examples of methods of quantitative analysis based on data acquired in this manner include Ratio (also referred to as "P-B ratio" or "peak to background ratio"), fluorescence recovery after photo bleaching (FRAP), fluorescence resonance energy transfer (FRET), and the like. Details on the aforementioned methods can be found in the following:

(1) Rajesh Babu Sekar and Ammasi Periasamy, "Fluorescence resonance energy transfer (FRET) microscopy imaging of live cell protein localizations", The Journal of Cell Biology, Volume 160, Number 5, Mar. 3, 2003:629-633
(2) Richard N. Day and Fred Schaufele, "Imaging Molecular Interactions in Living Cells", Endocrine Society, Molecular Endocrinology, July 2005, 19(7):1675-1686
(3) Peter F. Davies, Jenny Zilberberg, Brian P. Helmke, "Spatial Microstimuli in Endothelial Mechanosignaling", American Heart Association, Journal of the American Heart Association, Circulation Research 2003; 92:359-370

However, with STORM images generated on the basis of position information of the fluorescent material contained in the observation sample, the bright spot information (number of photons, ellipticity, and the like) belongs to the position information (center-of-gravity coordinates). Therefore, the conventional method of quantitative analysis cannot be applied as-is to fluorescent images in which the intensity value (fluorescent light quantity) is acquired at the pixel level.

To answer this problem, an analysis method which allows the quantification of the states of fluorescent images containing a plurality of bright spots and the carrying out of quantitative analysis in sample picture images of high resolution is described in the techniques shown in the embodiments below.

In the following descriptions, the super-resolution microscope is a microscope that uses stochastic optical reconstruction microscopy (STORM).

In generally known STORM technology, it is possible to acquire a sample picture image of high resolution, but the sample picture image is generated on the basis of fluorescent bright spots in the plurality of fluorescent images detected discretely on the time axis, and a plurality of fluorescent images detected within a predetermined period of time are needed in order to acquire one sample picture image.

In STORM, positions of the fluorescent bright spots are computed by calculating the luminosity distribution in the fluorescent image.

In other words, STORM computes the positions of the fluorescent bright spots on the basis of data obtained optically and increases the resolution at which the positions of the fluorescent bright spots are shown.

As a consequence, in typical STORM, in order to acquire one sample picture image, the positions of the fluorescent bright spots are computed from a plurality of fluorescent images detected at different points of time. With regards to the computation of the positions of the fluorescent bright spots, it is known that the resolution of the acquired sample picture image increases when the number of fluorescent images is increased. However, in STORM types that probabilistically compute the positions of the fluorescent bright spots on the basis of luminosity distribution, when the number of fluorescent images is increased in order to increase the resolution, the time necessary to acquire one sample picture image increases and the computation load also increases. On the other hand, when the number of fluorescent images is reduced in an effort to shorten the interval between acquired sample picture images, it becomes impossible to attain the necessary resolution.

A technique is described hereinafter that enables the performance of quantitative analysis on sample picture images of high resolution, while overcoming the problems associated with generally known STORM types as described above.

In the following analysis method for sample picture images of high resolution, a plurality of fluorescent images containing bright spots caused by irradiating a sample with excitation light are acquired, and analysis is carried out on the basis of sample picture images that show the positions of the bright spots computed from image information showing the fluorescent image. Additionally, in this analysis method, on the basis of the position information computed as the positions of bright spots in the sample picture image, predetermined areas that contain the positions of said bright spots are set as areas corresponding to said bright spots.

Note that the present embodiment is intended to explain the summary of the invention in detail so that it can be better understood, and does not limit the present invention unless otherwise specified. In addition, in the drawings used in the following explanation, main sections may be shown in an enlarged manner for the sake of convenience so that the features can be easily understood. Accordingly, the scale or the like of each requested element is not necessarily the same as the actual scale.

FIG. 1 is a configuration diagram illustrating a microscope device according to the present embodiment.

The microscope device 10 includes a light source 12, a control unit 14, a microscope main body 15, a storage unit 16, and a display unit 17.

In the present embodiment, the microscope device 10 is a microscope device that uses super-resolution microscopy (Stochastic Optical Reconstruction Microscopy: STORM). In the microscope device 10, a sample labeled with a fluorescent material is used. This fluorescent material emits fluorescence and becomes inactive upon irradiation with excitation light L1 while in an active state. The fluorescent material has properties by which, after emitting fluorescence upon irradiation with the excitation light L1 and becoming inactive, the fluorescent material becomes reactivated upon irradiation with activation light L2 of a wavelength that differs from that of the excitation light L1. Using the excitation light L1 and the activation light L2, operations are repeated wherein discretely distributed fluorescence is observed by causing light emission of only a portion of the fluorescent material in the sample. As a result, a sample picture image is formed using the numerous acquired fluorescent images.

The light source 12 according to the present embodiment includes an excitation illumination system 11 and an activation illumination system 13.

The excitation illumination system 11 is provided with a laser light source 21, a shutter 22, and a total reflection mirror 32. The excitation illumination system 11 is connected to the microscope main body 15 via the total reflection mirror 32.

The laser light source 21 is a light source which supplies the excitation light L1 to the microscope main body 15 for the purpose of causing the fluorescent material adhered to the sample to emit light. It is sufficient that the laser light source 21 emit the excitation light L1 of a wavelength adapted to the fluorescent material contained in the sample. For example, depending on the type of fluorescent material, a green laser (wavelength: 532 nm), a red laser (wavelength: 633 nm, 657 nm), a violet laser (wavelength: 405 nm), a blue laser (wavelength: 457 nm), or the like may be used.

The shutter 22 is a device which conducts changeover between supply and stoppage of the excitation light L1 to the microscope main body 15. For example, the shutter 22 may be configured to be provided with a light shielding member that blocks the excitation light L1 emitted from the laser light source 21, and a drive apparatus that advances and retracts the light shielding member relative to and from the optical path of the excitation light L1.

Alternatively, an acousto-optic tunable filter (AOTF) may be used as the shutter 22. The total reflection mirror 32 serves to totally reflect the excitation light L1 radiated from the laser light source 21 toward a stage 31 (described hereinafter) of the microscope main body 15.

Based on the description above, the excitation illumination system 11 is configured to radiate the excitation light L1 to all areas of the observation view field (observation area) on the stage 31.

On the other hand, the activation illumination system 13 is provided with a laser light source 42, a scanner 43, and a dichroic mirror 33. The activation illumination system 13 is connected to the microscope main body 15 via the dichroic mirror 33 being inserted on the optical path of the excitation light L1. The dichroic mirror 33 serves to reflect the activation light L2 radiated from the laser light source 42 toward the stage 31 and transmit the excitation light L1 toward the stage 31.

The laser light source 42 radiates the activation light L2 toward the microscope main body 15 for purposes of activating the fluorescent material. It is sufficient that the laser light source 42 emit the activation light L2 of a wavelength adapted to the fluorescent material contained in the sample. For example, depending on the type fluorescent material, a green laser (wavelength: 532 nm), a red laser (wavelength: 633 nm, 657 nm), a violet laser (wavelength: 405 nm), a blue laser (wavelength: 457 nm), or the like may be used.

The scanner 43 scans the activation light L2 on the stage 31 of the microscope main body 15. For example, a biaxial galvano scanner may be used as the scanner 43. Based on the description above, the activation illumination system 13 is configured to enable irradiation of the observation view field (observation area) on the stage 31 with the activation light L2 while scanning is conducted by the scanner 43.

Note that a laser light source apparatus provided with the laser light source 21 and the laser light source 42 within a single housing, and configured to be capable of radiating multiple types of laser light may be used as the light source 12. In the case where this type of laser light source apparatus is provided, both the excitation light L1 and the activation light L2 can be supplied to the microscope main body 15 from a single illumination system by configuring an illumination system that is provided with the shutter 22 and the scanner 43 along with the laser light source apparatus.

The microscope main body 15 may, for example, be configured from an inverted microscope. The microscope main body 15 is provided with the stage 31 on which the observation target, or sample, is placed. Additionally, a camera 34 for photographing fluorescent images of the sample placed on the stage 31 is connected to the microscope main body 15. The camera 34 may, for example, be a CCD camera having numerous pixels.

Although not illustrated in the drawings, the microscope main body 15 is also provided with an objective lens that irradiates the stage 31 with the excitation light L1 and the activation light L2, an image forming lens that couples the fluorescence (observation light) emitted from the fluorescent material in the sample to a light receiving surface of the camera 34, and the like. The objective lens and the image forming lens described above are configured as the image-forming optical system of the present invention by which the sample placed on the stage 31 is observed.

The stage 31 is configured to enable total reflection illumination that causes total reflection of the excitation light L1 and the activation light L2 at the interface of the sample and a cover glass affixed to the sample.

Figure 2:
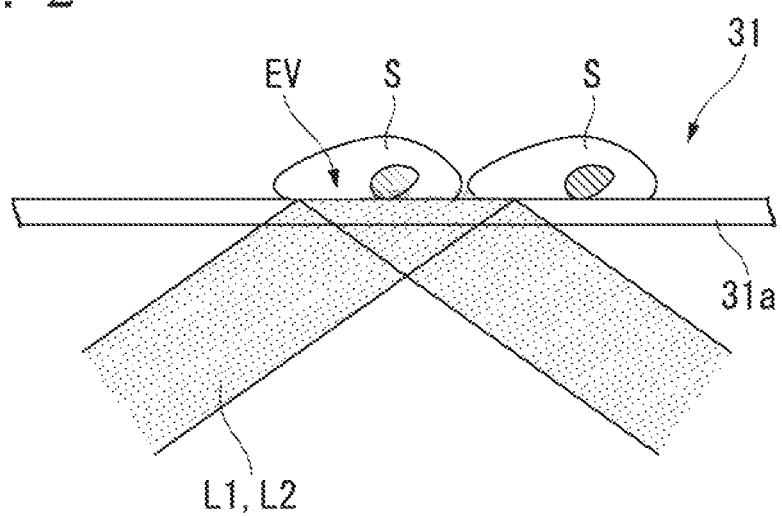
FIG. 2 is a schematic drawing of total reflected illumination.

FIG. 2 is an explanatory drawing illustrating a case where a sample S is irradiated with the activation light L2 (or the excitation light L1) via total reflection illumination. As illustrated in FIG. 2, as a result of total reflection illumination, the sample S can be illuminated by the evanescent light EV that exudes from the cover glass 31a to the sample side when the illumination light (the excitation light L1 or the activation light L2) is totally reflected. As the range that evanescent light travels is limited to a range on the order of 100 to 150 nm from the interface, only the fluorescent material positioned in the vicinity of the cover glass 31a surface can be induced to emit light, and this can be achieved with a high S/N ratio by markedly mitigating background fluorescence.

The microscope main body 15 of the present embodiments has a configuration that enables use by switching between the total reflection illumination described above and epi-illumination.

Returning to FIG. 1, the control unit 14 described above is a computer that comprehensibly controls the microscope device 10, and is connected to the storage unit 16, the display unit 17, and a camera controller 19. In the present embodiments, the control unit 14 has at least a control signal generation function that generates control signals for purposes of controlling these devices, a fluorescent image acquisition unit 141 that acquires fluorescent images via the camera controller 19, a picture image forming unit 142 that generates a sample picture image from a plurality of fluorescent images, and a sample picture image analysis unit 143 that performs an analysis based on the generated sample picture image.

Additionally, the sample picture image analysis unit 143 is provided with an area setting unit 143A and an analysis processing unit 143B. The area setting unit 143A sets predetermined areas relative to the bright spots on the basis of the sample picture image generated by the picture image forming unit 142. The analysis processing unit 143B performs quantitative analysis processing based on the image information representing the predetermined areas set at each of the bright spots by the area setting unit 143A. Ratio or FRAP, for example, may be included as the quantitative analysis processing. Next, a description of the specific processing carried out by sample picture image analysis unit 143 shall be given.

The storage unit 16 is composed, for example, of a semiconductor memory, a hard disk, or the like, and stores a program used in the control unit 14 and data (fluorescent images and the like) supplied from the control unit 14 in a manner that allows read-out from the control unit 14. Note that when performing the analysis processing of the present embodiments, for each of the bright spots, the storage unit 16 associates and stores position information showing the position of the bright spot and information showing the state of the bright spot (numerical value or the like) with identification information that identifies the bright spot, and also stores information showing the area associated with the bright spot.

The display unit 17 is, for example, a monitor (display device) or a printer (printing device), and provides functions for displaying and/or printing images based on the picture image data outputted from the control unit 14. In the present embodiments, the display unit 17 is a monitor.

The camera controller 19 conducts drive control of the camera 34 connected to the microscope main body 15.

The camera controller 19 operates the camera 34 on the basis of control signals inputted from the control unit 14, acquires picture images of the fluorescence radiated from the sample, and outputs the acquired fluorescent images to the control unit 14.

The microscope device 10 implements the various types of operations which are required to execute the image processing method described below by performing in combination the functions provided to the control unit 14 described above. Accordingly, the microscope device 10 is additionally provided with a sample picture image generating device that generates a fluorescent image through STORM photograph processing and image processing, specifically by generating a fluorescent image containing the plurality of bright spots by displaying the positions of the images of the fluorescent material contained in the acquired fluorescent image as bright spots; and a sample picture image analysis device that performs an analysis based on the generated sample picture image.

Next a description is given of an example of the picture image analysis method of the present invention, on the basis of a description of the operation of the microscope device 10. The microscope device 10 performs picture image analysis on captured sample picture images using super-resolution microscopy technology.

Figure 3:
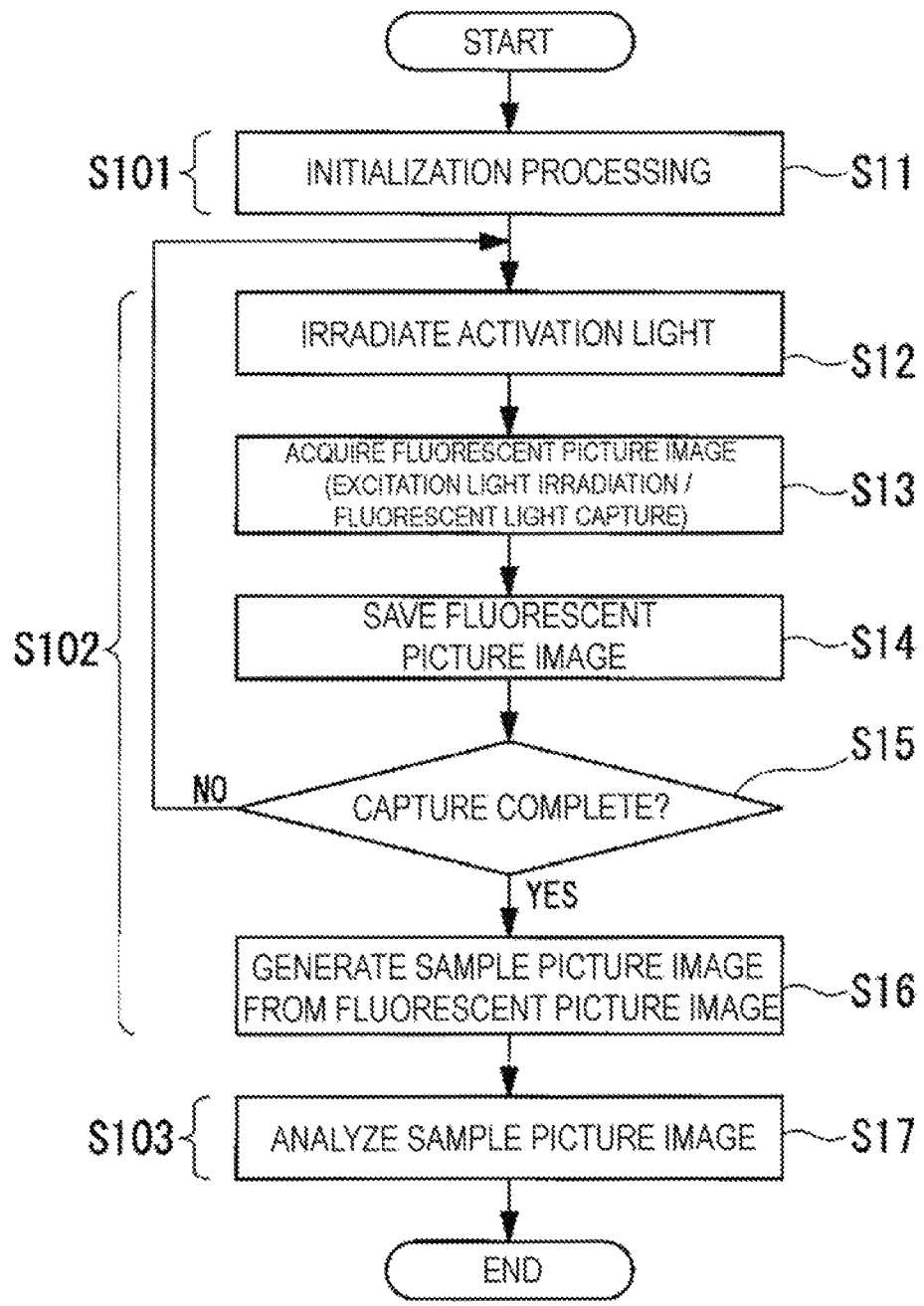
FIG. 3 is a flowchart showing an observation method according to the first embodiment.

FIG. 3 is a flowchart showing the image processing method of the present embodiment. Hereinafter, the image processing method according to the present embodiment will also be described within the context of the description of the image observation method of the microscope device 10.

The image processing method is composed of an initialization process step S101, a sample picture image generation step S102, and a sample picture image analysis step S103.

The initialization process step S101 includes a step S11 in which initialization processing required for later observation processing with the microscope device 10 is performed. Additionally, the sample picture image generation step S102 includes a step S12 in which the observation view field is irradiated with the activation light L2; a step S13 in which, following irradiation with the activation light L2, the observation view field is irradiated with the excitation light L1 and a second fluorescent image is acquired; a step S14 in which the second fluorescent image is saved; a step S15 in which capture completion is determined; and a step S16 in which a sample picture image is generated from a plurality of the second fluorescent images.

Additionally, the sample picture image analysis step S103 includes a step S17 in which an analysis based on the STORM image (sample picture image) is performed and, on the basis of the position information computed as the positions of bright spots in the STORM image, predetermined areas that contain the positions of said bright spots are set as areas corresponding to said bright spots.

A summary of the image observation procedure using the microscope device 10 is given below.

First, in the initialization process step S101, initialization processing is completed. Thereafter, in the sample picture image generation step S102, an operation of irradiating the sample with the activation light L2 and an operation of irradiating the sample with the excitation light L1 to acquire the second fluorescent image are repeated hundreds to tens-of-thousands of times (STORM capture processing). Then, a STORM image of high resolution is acquired by synthesizing the multiple second fluorescent images that were captured.

Figure 4:
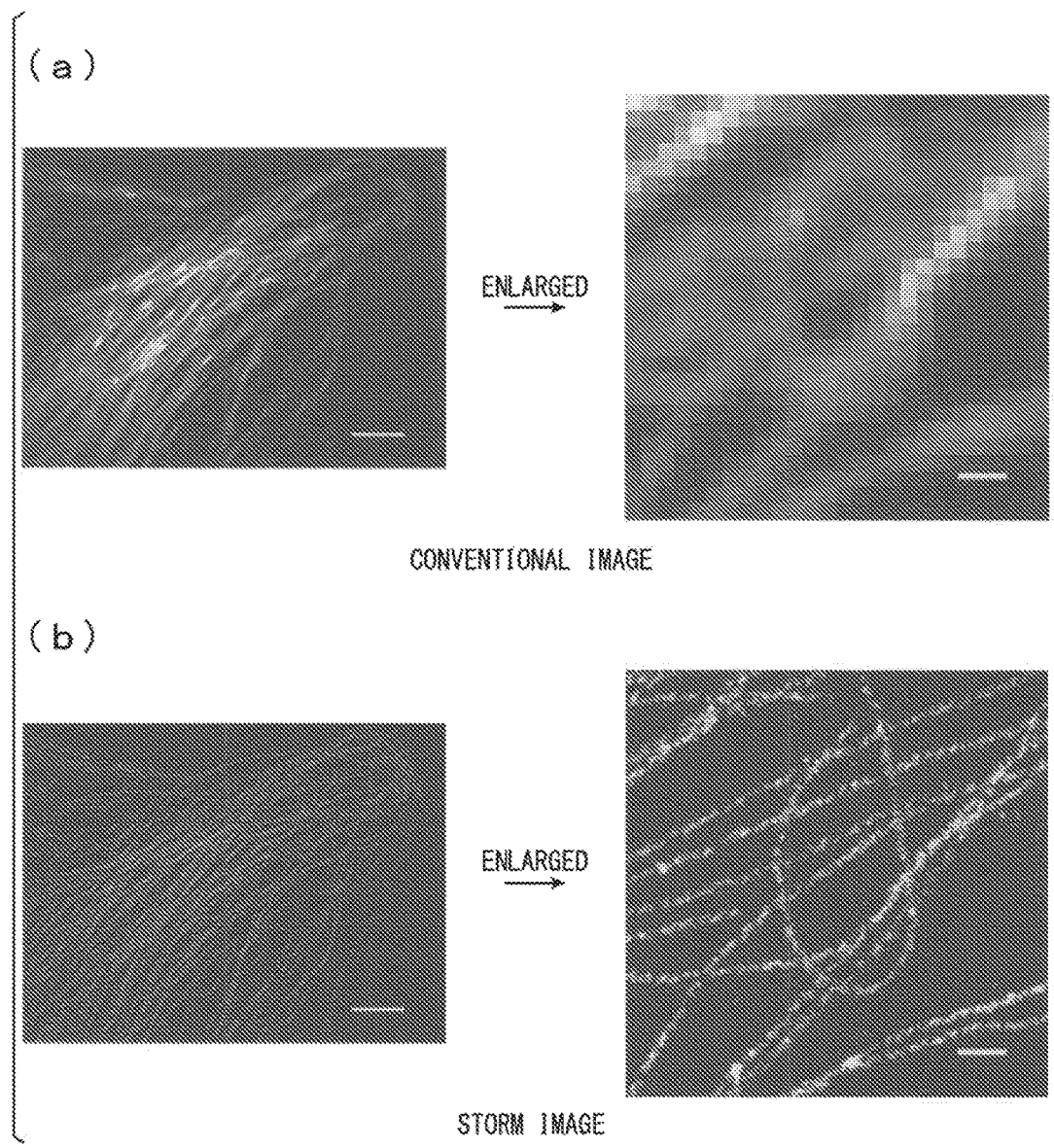
FIG. 4 is a drawing comparing a conventional image and a STORM image.
Figure 5:
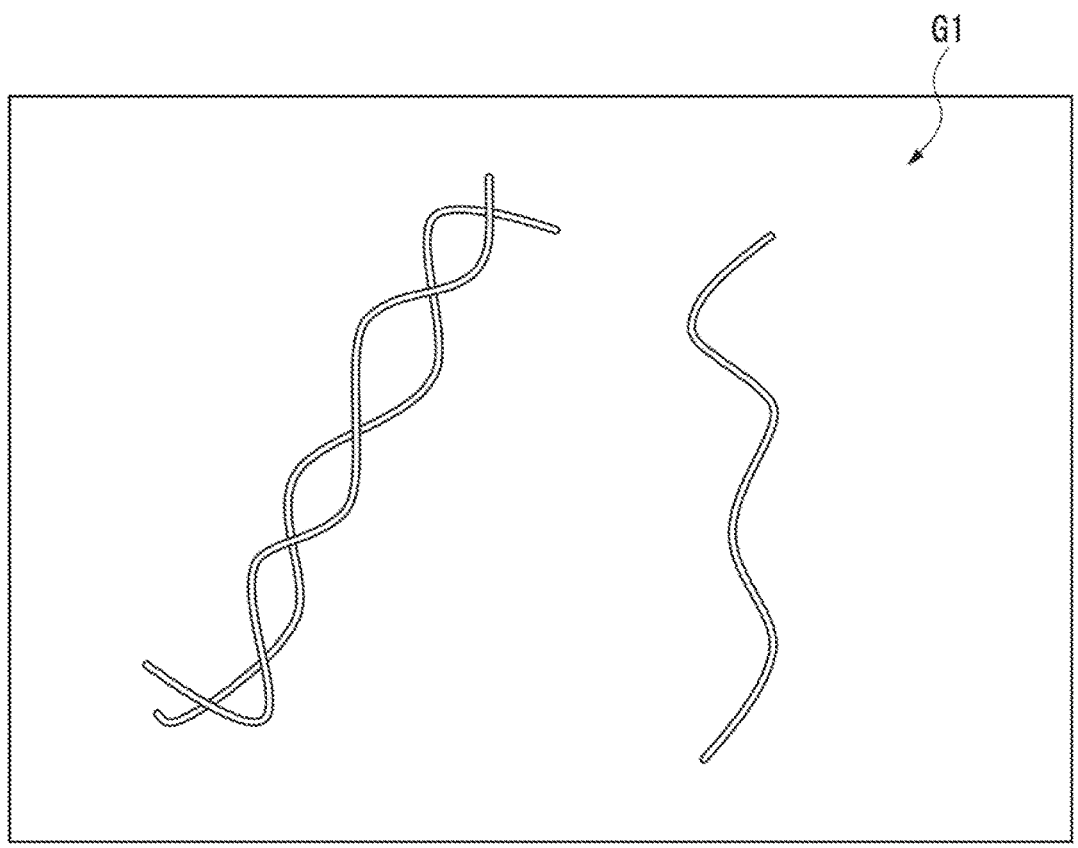
FIG. 5 is a schematic drawing conceptually illustrating a conventional image.
Figure 6:
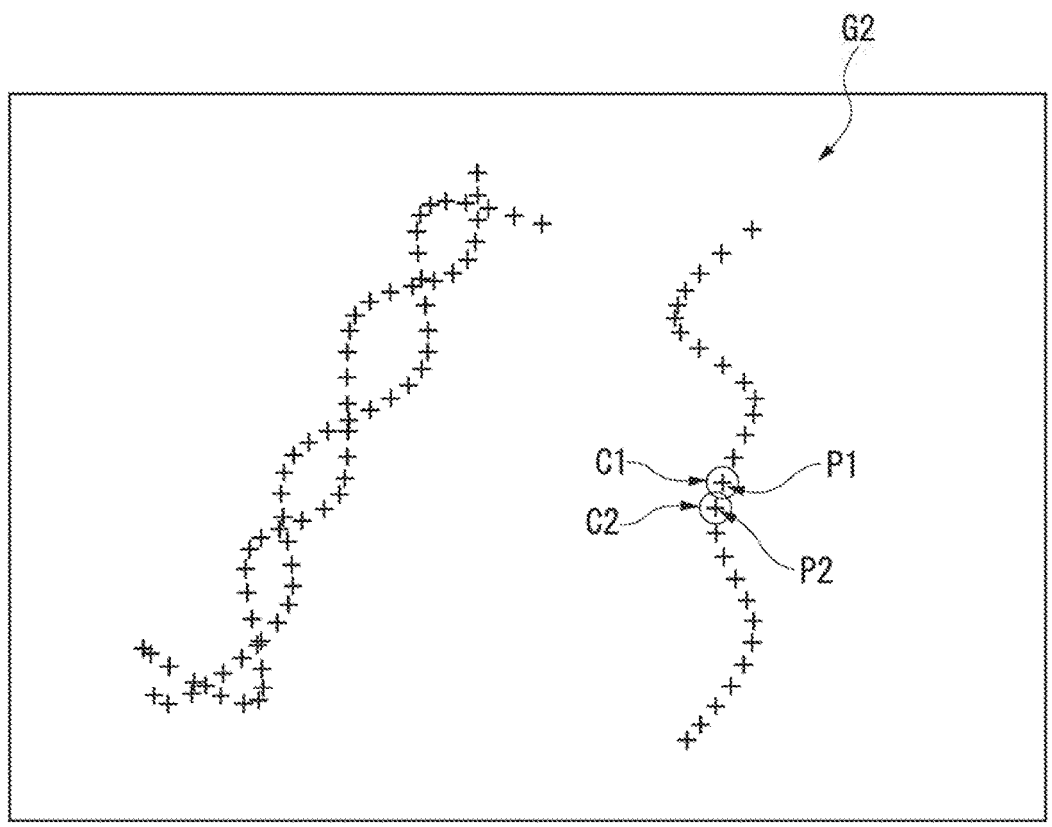
FIG. 6 is a schematic drawing conceptually illustrating a STORM image.

The difference between images observed without the use of super-resolution microscopy technology (conventional image) and STORM images acquired in sample picture image generation step S102 is described below while referencing FIG. 4 to FIG. 6. FIG. 4 is a drawing that compare an image observed without the use of super-resolution microscopy technology (conventional image) and a STORM image acquired in the sample picture image generation step S102. Part (a) of FIG. 4 illustrates an example of a conventional image, and part (b) of FIG. 4 illustrates an example of a STORM image. FIG. 5 is a schematic drawing conceptually illustrating a conventional image, and FIG. 6 is a schematic drawing conceptually illustrating a STORM image.

As illustrated in FIG. 4(a), in the conventional image, fine portions beyond the optical resolution limit cannot be imaged. As illustrated in FIG. 5, the detection target shown via conventional imaging is shown as a continuous line.

However, as illustrated in FIG. 4(b), the STORM image acquired via STORM image processing is an image displaying detected results at a resolution higher than that in the conventional image. As illustrated in FIG. 6, discretely distributed bright spots are shown.

In order to solve the problems described above, with the microscope device 10 according to the present embodiments, after the sample picture image generation step S102, analysis processing is performed on the basis on the STORM image (sample picture image) in the sample picture image analysis step S103. For example, on the basis of the position information computed as the positions of bright spots in the STORM image, the area setting unit sets predetermined areas that contain the positions of said bright spots as areas corresponding to said bright spots.

Principals Common Throughout the Embodiments

The principals for performing the analysis from the STORM image (sample picture image) in the present embodiments are described below while referencing FIG. 6 described above.

Bright spot P1 and bright spot P2 are shown in FIG. 6. It would be understood to a human observer of the sample picture image that the bright spot P1 and the bright spot P2 are in a relationship adjacent to each other.

However, from the position information (coordinate positions) of each of the bright spot P1 and the bright spot P2, one can only discern that the bright spots are disposed so as to be separated a certain distance from each other. In some cases, the bright spot P1 and the bright spot P2 showing in the sample picture image may not be objects detected as spots in the same fluorescent image, but may show, in the sample picture image, as points in a line which were derived from data detected at different times.

In the event that each of these spots had moved, it would be difficult to determine from the data whether the spot detected first had moved, a different spot had moved or, moreover, if the second detected spot was a new spot altogether.

In order to solve this problem, the following processing is performed in order on each of the bright spots in the sample picture image generated by STORM. Thereby, predetermined areas C1 and C2 respectively corresponding to the bright spots P1 and P2 are associated with the bright spots P1 and P2. Although not illustrated in the drawings, the association of the areas is performed on all of the bright spots in the sample picture image.

First, a specific bright spot is established as a reference point. Hereinafter, the phrase "near the bright spot" means "a range within prescribed conditions, referenced from the position of the bright spot". For example, the range of "near the bright spot" may be defined on the basis of the position of the bright spot in space. In this case, the range may be identified as a predetermined area determined by distance from the bright spot. Accordingly, in a case where the predetermined area is defined as a sphere, the diameter of the sphere, from 10 nm to 200 nm, for example, is set as the range.

In other words, the predetermined range can be defined as a spatial window having a range from the position of the reference bright spot to a prescribed predetermined distance.

Additionally, "near the bright spot" may, for example, be defined in terms of an interval of time from the moment of detection of a bright spot. In this case, if the moment of detection of the bright spot is defined as the point of origin (starting point) on the time axis, the interval of time from the moment of detection of the bright spot can be identified as the time-lapse from the starting point. Additionally, the range of the time-lapse that determines "near the bright spot" can be defined as a "period". "Near the bright spot" is preferably set, for example, as a range from a period of 1 ms from the detection of the bright spot to a period of 10 ms from the same. In other words, it can be said that with regards to the aforementioned period, a time window is set having an effective detection range starting with the detection of a particular bright spot and ending upon the passage of the aforementioned period.

Within this period, a plurality of STORM fluorescent images are detected, and at least one sample picture image is generated on the basis of the fluorescent images in this period.

A value will be identified that represents the state of the spatial area (two-dimensional, three-dimensional) determined by the predetermined area in space and the period on the time axis as previously defined. By identifying a value that represents the state of the defined spatial area, a quantitative comparison can be carried out, even in cases where results are detected based on differing states. Examples of the aforementioned differing states includes cases where the range of detection includes the same predetermined area in space and the same predetermined period on the time axis, but differing spectral bands; cases where detection is carried out in a different predetermined area in space; cases where detection is carried out in a different period on the time axis; and the like. Additionally, through this method of quantitative comparison, for example, the difference in integrated values detected on the basis of differing states can be found, or ratios can be found. As a result, a concrete evaluation value can be computed. In cases where this evaluation value is a predetermined range determined spatially or temporally, even when the integrated values are detected under differing conditions (e.g. position, time, wavelength, and the like), in cases where the difference from the information computed from the previously detected sample picture image is small, it can be presumed that the same sample has been detected.

As such, by defining the predetermined areas based on the bright spots in the sample picture image as described above, analysis processing based on the specified image information can be performed.

Next, conditions common throughout the description of the embodiments below are set forth while referencing FIG. 7.

Figure 7:
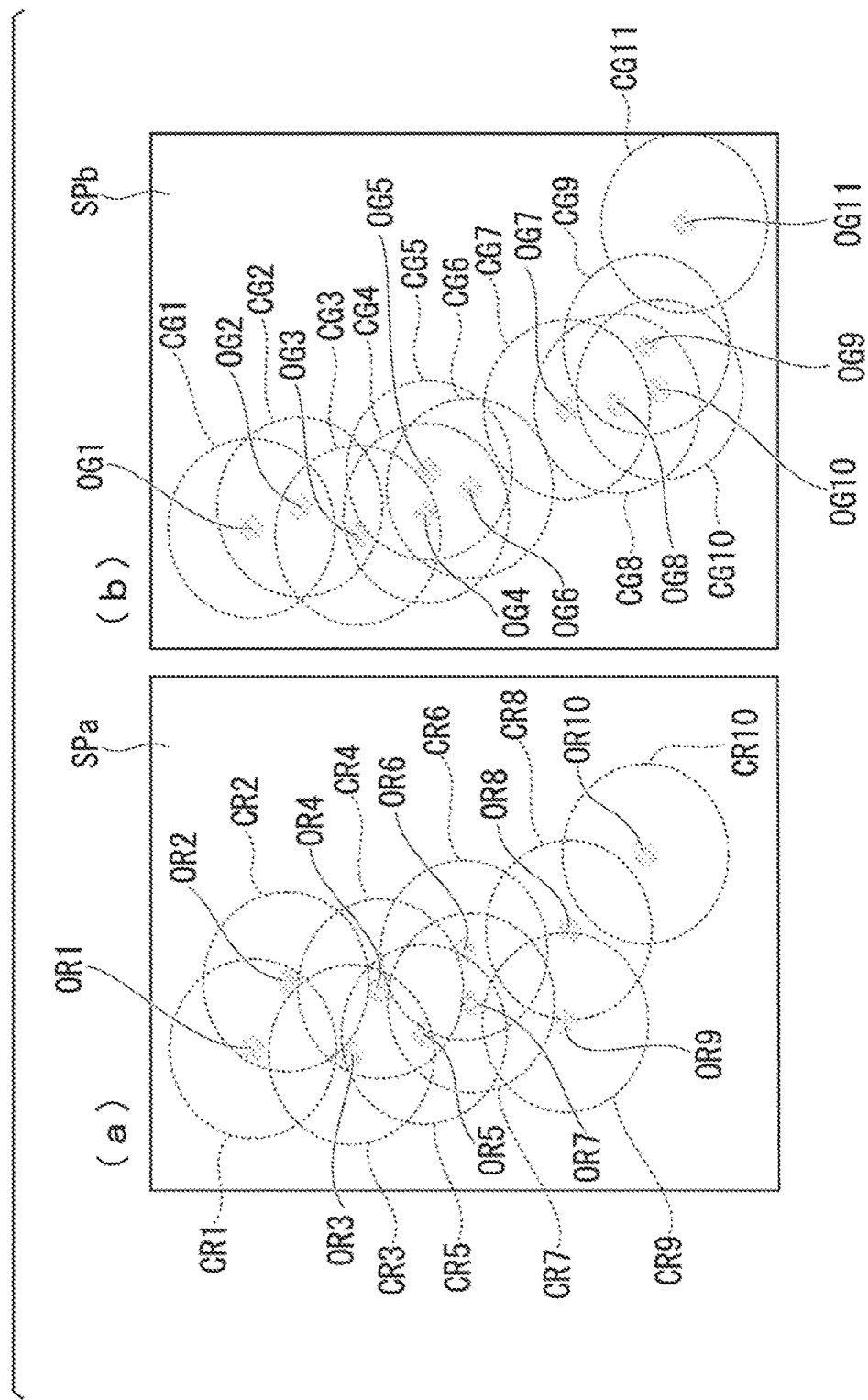
FIG. 7 is a drawing illustrating bright spots in a STORM image.

FIG. 7 is a drawing illustrating bright spots in a STORM image. The target ranges shown in FIG. 7 is explained as showing three-dimensional space. However, this should not be construed as a limitation to processing on a two-dimensional plane.

The two drawings of parts (a) and (b) in FIG. 7 show sample picture images detected under the following states: the same predetermined area in space, the same period, and differing spectral bands of light. For example, FIG. 7(a) shows an area where the wavelength band of light of the sample picture image SPa is greater than or equal to 530 nm or, in other words, an area where the wavelength is longer than that of green light; and FIG. 7(b) shows an area where the wavelength band of light of the sample picture image SPb is less than 530 nm or, in other words, an area where the wavelength is shorter than that of green light. In the following description as well, in each drawing described, 530 nm is set as the threshold and part (a) shows an area where the wavelength band of light of the sample picture image SPa is greater than or equal to 530 nm, and part (b) shows an area where the wavelength band of light of the sample picture image SPb is less than 530 nm.

Positions (coordinates) indicated by reference characters OR1 to OR10 in FIG. 7(a) show the positions (coordinates) of each individual bright spot. Reference characters CR1 to CR10 indicate predetermined areas in space based on each individual bright spot OR1 to OR10. FIG. 7(a) shows a case where the predetermined areas are shown as spheres (circles). Additionally, positions indicated by reference characters OG1 to OG11 in FIG. 7(b) show the positions of each individual bright spot. Reference characters CG1 to CG11 indicate predetermined areas in space based on each individual bright spot OG1 to OG11. FIG. 7(b) shows a case where the predetermined areas are shown as spheres (circles).

In a comparison of part (a) and part (b) in FIG. 7, it is clear that the number and position of the detected bright spots is different. Furthermore, in parts (a) and (b) of FIG. 7, due to the differing of the position of each of the bright spots, it is clear that the distance between the bright spots, detected under the same states with the exception of the wavelengths, also differs.

As shown in FIG. 7(a) and FIG. 7(b), the sample picture image analysis unit 143 (FIG. 1) sets predetermined areas containing the positions of the bright spots as areas in accordance with the bright spots, corresponding to the positions of the bright spots in each sample picture image. Position information (coordinate information) of the bright spot and information showing the state of the bright spot are associated with each of the bright spots and stored in storage unit 16. The sample picture image analysis unit 143 sets a value based on the information showing the state of the bright spot to be the value representing the state of the predetermined area.

The sample picture image analysis unit 143 treats the area within a prescribed radius, having the position shown by the position information as the center, as the predetermined area. For example, as described in the following embodiments, the predetermined area described above is associated with a plurality of unit cells that are smaller than the size of the predetermined area. As a result, it is possible to perform an analysis at a resolution determined by the size of the unit cells. The sample picture image analysis unit 143 may apply Ratio, FARP, or other analysis methods as the analysis at a resolution determined by the size of the unit cells.

Hereinafter, different aspects of the invention will be listed in order as individual embodiments, but the conditions shown in the sample picture images described above shall be construed to be common throughout the embodiments.

First Embodiment

An aspect of the present embodiment, in which areas corresponding to bright spots are set based on positions of the bright spots in a STORM image, will be described while referencing FIG. 8.

Figure 8:
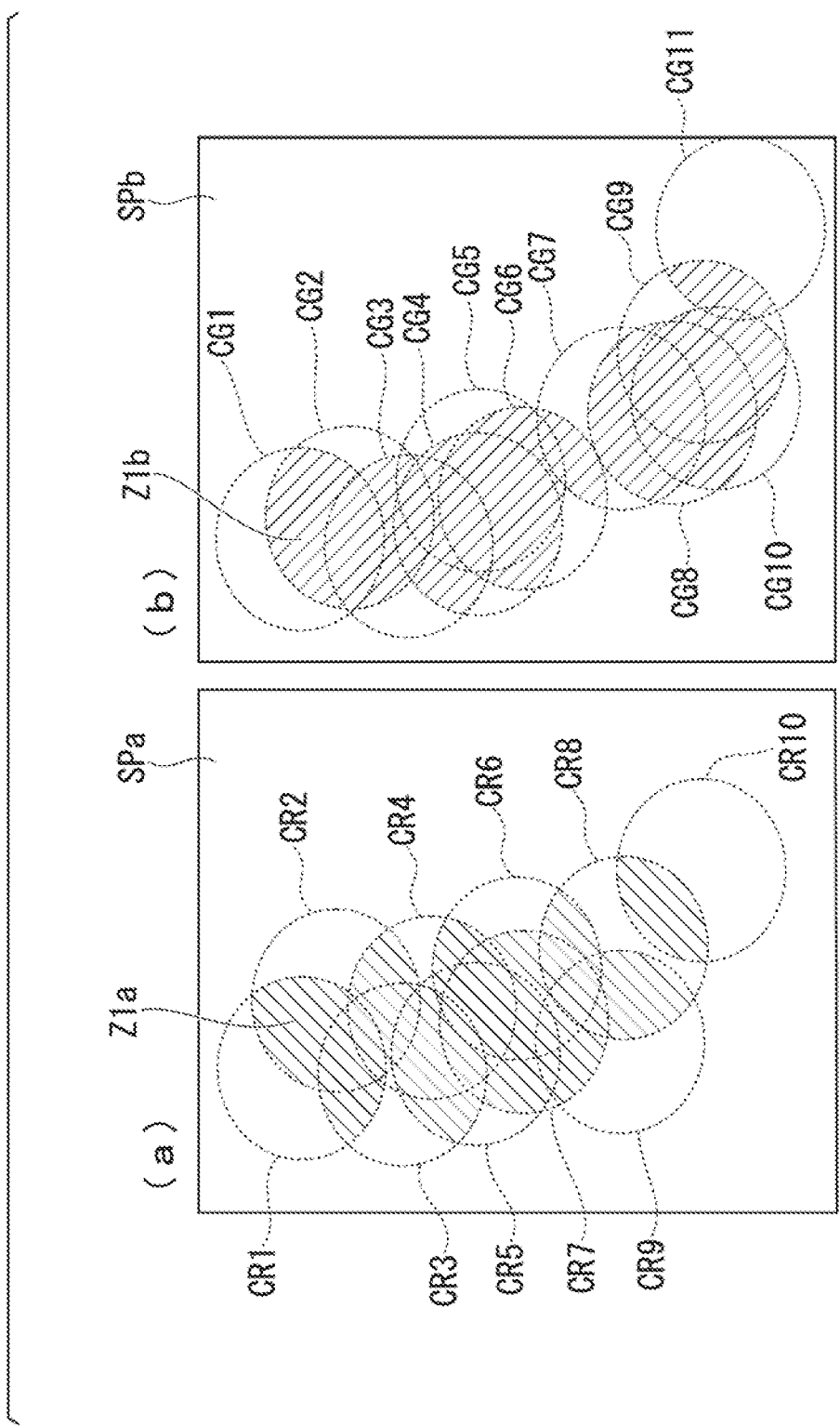
FIG. 8 is a drawing illustrating a method of setting areas corresponding to bright spots in a STORM image in the first embodiment.

FIG. 8 is a drawing illustrating a method of setting areas corresponding to bright spots in a STORM image in the present embodiment.

In the present embodiment, a sample picture image is analyzed in accordance with the rules described below as setting method 1.

(Setting Method 1: Case where Predetermined Areas are Filled in with Predetermined Values (Uniformly Filling in Spheres with a Value Representing the State of a Single Bright Spot in Each Sphere))

In the present embodiment, a case is described where a predetermined value is allocated to each of the predetermined areas.

Rule 1: First, a prescribed predetermined constant is set as a value that represents the state of a single bright spot associated with each predetermined area (sphere). For example, the intensity (number of photons) of the fluorescent image forming the bright spot or, rather, a numerical value proportional to the number of photons of the bright spot may be set as the value representing the state of the bright spot.

Rule 2: The value representing the state of the single bright spot, associated with each predetermined area (sphere), is allocated to a set area within each of the spheres shown as a predetermined area.

Rule 3: Next, in cases where there is a plurality of the predetermined areas (spheres) and the predetermined areas (spheres) have an overlapping portion, the sum of the numerical values allocated to each of the overlapping predetermined areas (spheres) in Rule 2 is calculated, and the resulting sum is newly allocated as the value of the overlapping area of the predetermined areas (spheres).

In part (a) of FIG. 8, area Z1a, marked by hatching angled down and to the left, is an area where two or more predetermined areas (spheres) of spheres overlap. In part (b) of FIG. 8, area Z1b, marked by hatching angled down and to the right, is an area where two or more predetermined areas (spheres) of spheres overlap. In a comparison of the area Z1a of FIG. 8(a) and the area Z1b of FIG. 8(b), it is clear that the positions of each of the areas differ, thus showing that quantitative analysis can be performed easier.

According to these rules, given that the number of photons of the bright spots is uniform, the size of the area where the predetermined areas (sphere) overlap will appear different, depending on the distance between the bright spots. In other words, the value allocated to each area will vary according to the density at which the bright spots are present.

By carrying out processing in accordance with this rule, space can be processed as a predetermined area (sphere) of desired size. Desired resolution information can be acquired by dividing space into smaller pieces. However, due to the amount of data increasing with the number of divisions, this processing is suited for cases where the area, or analysis target, is comparatively narrow.

For example, when analyzing a sample picture image in real-time in which the presence of two types of molecules varies from moment to moment, grouping in a range having a diameter of 50 nm is preferable.

Second Embodiment

An aspect of the present embodiment, in which areas corresponding to bright spots are set based on positions of the bright spots in a STORM image, will be described while referencing FIG. 9.

Figure 9:
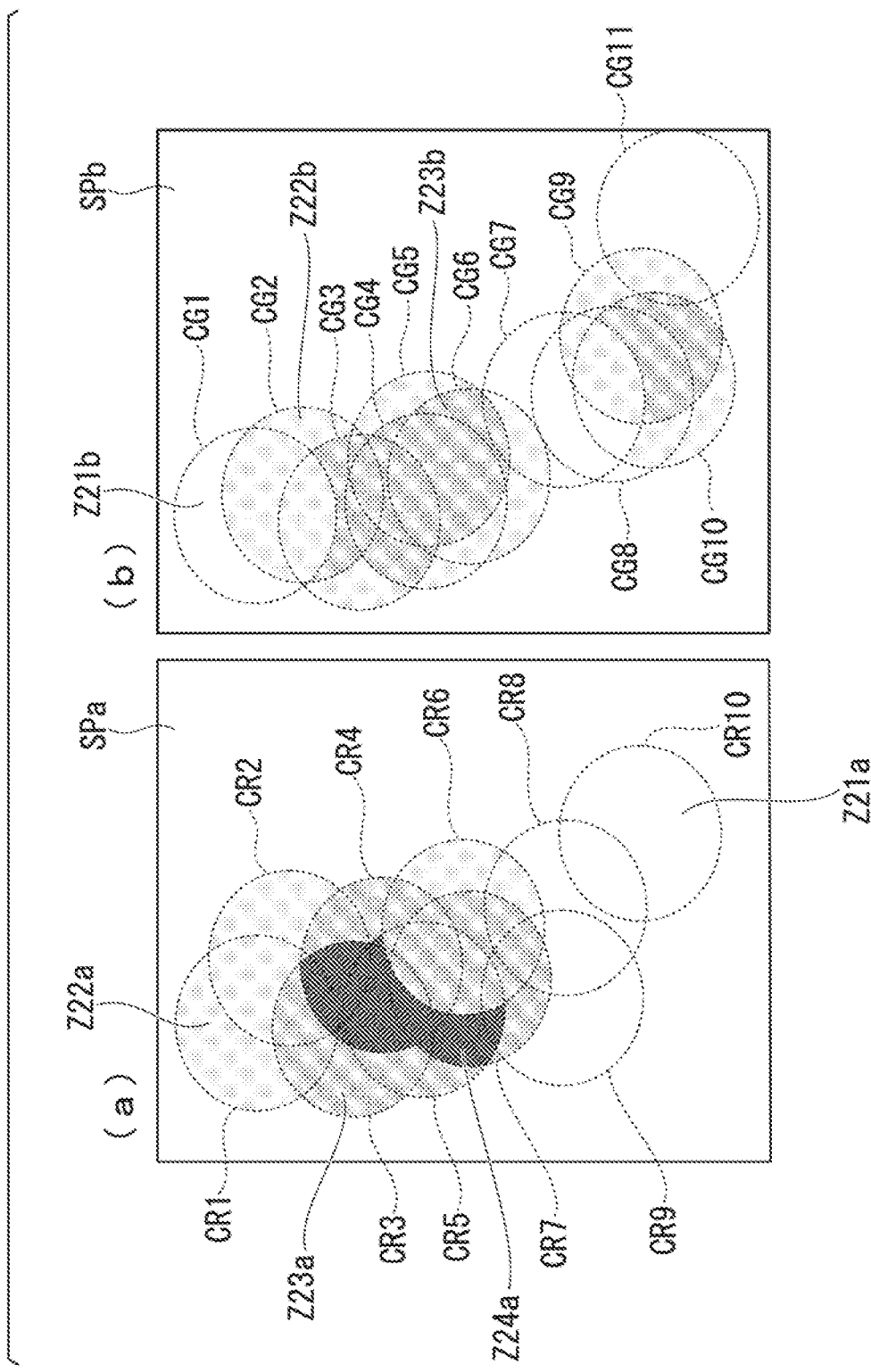
FIG. 9 is a drawing illustrating a method of setting areas corresponding to bright spots in a STORM image in a second embodiment.

FIG. 9 is a drawing illustrating a method of setting areas corresponding to bright spots in a STORM image in the present embodiment.

In the present embodiment, a sample picture image is analyzed in accordance with the rules described below as setting method 2.

(Setting Method 2: Case where Predetermined Areas (Spheres) are Filled in with Predetermined Values (Uniformly Filling in the Spheres with the Number of Bright Spots Contained in the Spheres))

In the present embodiment, a case is described where a predetermined value, in accordance with the number of the bright spots contained within each of the predetermined areas, is allocated.

Rule 1: First, a value representing the state of the bright spots contained in the predetermined area (sphere) is computed.

For example, a numerical value in accordance with the number of bright spots contained in the predetermined area (sphere) may be a value that represents the state of the bright spots contained in the predetermined area (sphere).

Rule 2: The value computed in Rule 1 is allocated to a set area within each sphere shown as a predetermined area.

Rule 3: Next, in cases where there is a plurality of the predetermined areas (spheres) and the predetermined areas (spheres) have an overlapping portion, the sum of the numerical values allocated to each of the overlapping predetermined areas (spheres) in Rule 2 is calculated, and the resulting sum is newly allocated as the value of the overlapping area of the predetermined areas (spheres).

In part (a) of FIG. 9, the areas showing three types of different shading (Z21a to Z24a) are areas where the values allocated to the predetermined areas (spheres) differ from each other. In part (b) of FIG. 9, the areas showing three types of hatching (Z21b to Z23b) are areas where the values allocated to the predetermined areas (spheres) differ from each other. In a comparison of part (a) and part (b) in FIG. 9, it is clear that the positions of each of the areas having their respective types of shading differ, thus showing that quantitative analysis can be performed easier.

According to these rules, the size of each of the predetermined areas can be made uniform, and the density of the bright spots in a predetermined area (sphere) can be expressed by the number of the bright spots contained in that area. For example, even in a case where the flickering time of the bright spots is varied, the impact caused by the variation in the flickering time can be mitigated, and thus quantitative analysis can be carried out, the variation in flickering time having been eliminated.

Third Embodiment

An aspect of the present embodiment, in which areas corresponding to bright spots are set based on positions of the bright spots in a STORM image, will be described while referencing FIG. 10.

Figure 10:
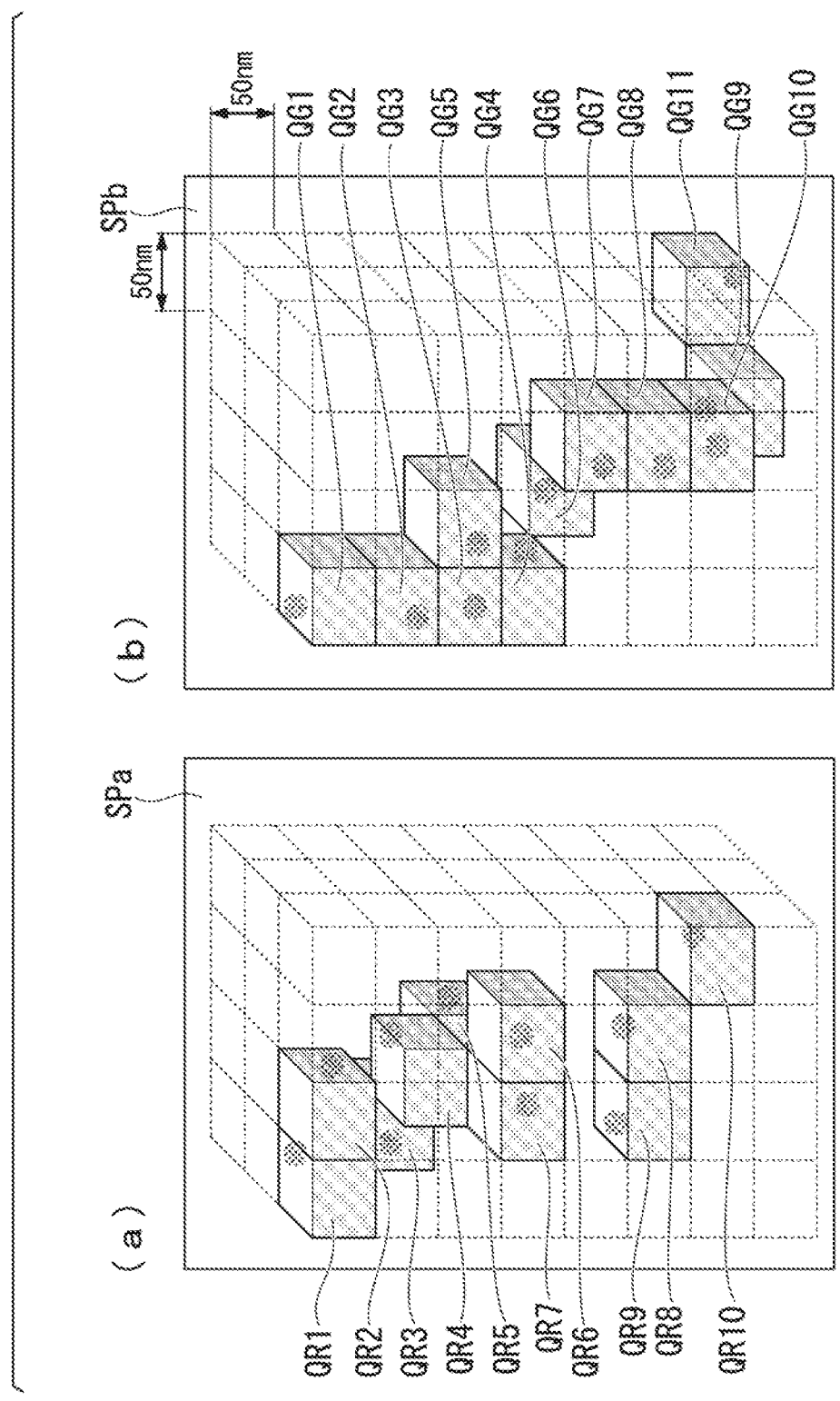
FIG. 10 is a drawing illustrating a method of setting areas corresponding to bright spots in a STORM image in a third embodiment.

FIG. 10 is a drawing illustrating a method of setting areas corresponding to bright spots in a STORM image in the present embodiment.

In the present embodiment, a sample picture image is analyzed in accordance with the rules described below as setting method 3.

(Setting Method 3: Case where a Predetermined Area is Divided into Cubes and Filled in with Predetermined Values (Uniformly Filling in the Cubes with Values Representing the States of the Bright Spots Contained in the Cubes))

In the present embodiment, a case is described where a predetermined value is allocated to each of the predetermined areas.

Rule 1: First, the area is divided by disposing cubes of a predetermined size.

Note that the cubes may be disposed at positions determined by a grid formed along orthogonal coordinates. The areas shown as divided cubes are defined as predetermined areas constituting an analysis unit. Note that by forming a grid along orthogonal coordinates, and making the intervals of the grid equal, the predetermined areas, shown as unit cells, will become cubes. For example, when analyzing a sample picture image (three-dimensional image) in real-time in which the presence of two types of molecules varies from moment to moment, the unit cells described above are configured to be cubes, a size thereof defined by a length of one edge being 50 nm.

Note that the grid need not have equal intervals and that the predetermined area may be configured to have any desired shape (random shape).

Additionally, the value that represents the state of the predetermined area is a prescribed predetermined constant. For example, the value that represents the state of the predetermined area may be a numerical value proportional to the number of photons of the bright spots (single bright spot or multiple bright spots) contained in the predetermined area or, alternatively, may be a numerical value proportional to the number of bright spots (single bright spot or multiple bright spots) contained in the predetermined area.

Rule 2: The values representing the states of the predetermined areas (cubes), are allocated to each set area shown as a predetermined area.

Note that in FIG. 10, results through Rule 2 are shown as oblique drawings.

In part (a) of FIG. 10, cubes labeled with reference numerals QR1 to QR10 are disposed in areas of a part of the grid. The position of each of the cubes QR1 to QR10 is determined according to the position of the bright spots having a wavelength within a specific range. The specific wavelength range in FIG. 10(a) is, for example, wavelengths greater than or equal to 530 nm. Here, according to the rules described above, predetermined numeric values are allocated to the cubes QR1 to QR10 in accordance with each of the bright spots, as the values representing the states of the predetermined areas. For example, the numeric values for the cubes QR1 to QR10 may be set, in order, as 2, 2, 3, 3, 3, 3, 2, 1, 1, and 1, respectively.

In part (b) of FIG. 10, cubes labeled with reference numerals QG1 to QG11 are disposed in areas of a part of the grid. The position of each of the cubes QG1 to QG11 is determined according to the position of the bright spots having a wavelength within a specific range. The specific wavelength range in FIG. 10(b) is, for example, wavelengths less than 530 nm. Here, according to the rules described above, predetermined numeric values are allocated to the cubes QG1 to QG11 in accordance with each of the bright spots, as the values representing the states of the predetermined areas. For example, the numeric values for the cubes QG1 to QG11 may be set, in order, as 2, 3, 3, 3, 3, 3, 2, 4, 3, 3, and 1, respectively.

In a comparison of part (a) and part (b) in FIG. 10, because the position of the area shown by each cube is determined according to the wavelength of the bright spot present in the unit cell, it is clear that the position of each cube differs according to the wavelength of the bright spot, and, it is understood that this facilitates the performance of quantitative analyses.

In accordance with these rules, the size of each of the predetermined areas is made uniform as the size of the unit cell or, rather, the cube. Thus, the value in accordance with the number of photons of the bright spots (single bright spot or multiple bright spots) assigned within this area or, alternatively, the numerical value proportional to the number of bright spots (single bright spot or multiple bright spots) contained in the predetermined area can be set.

By carrying out processing in accordance with this rule, space can be processed as a predetermined area (cube) of desired size. Desired resolution information can be acquired by dividing space into smaller pieces. However, due to the amount of data increasing with the number of divisions, this processing is suited for cases where the area, or analysis target, is comparatively narrow.

Additionally, in a comparison with conventional confocal images, data that is readily comparable can be generated by combining the pitch of the pixels of the confocal image with the pitch at which the cubes described above are disposed.

In the present embodiment, attention is paid to the fact that, in the generated information, the original signal shape (sphere) is replaced with a cube.

Fourth Embodiment

An aspect of the present embodiment, in which areas corresponding to bright spots are set based on positions of the bright spots in a STORM image, will be described while referencing FIG. 11.

Figure 11:
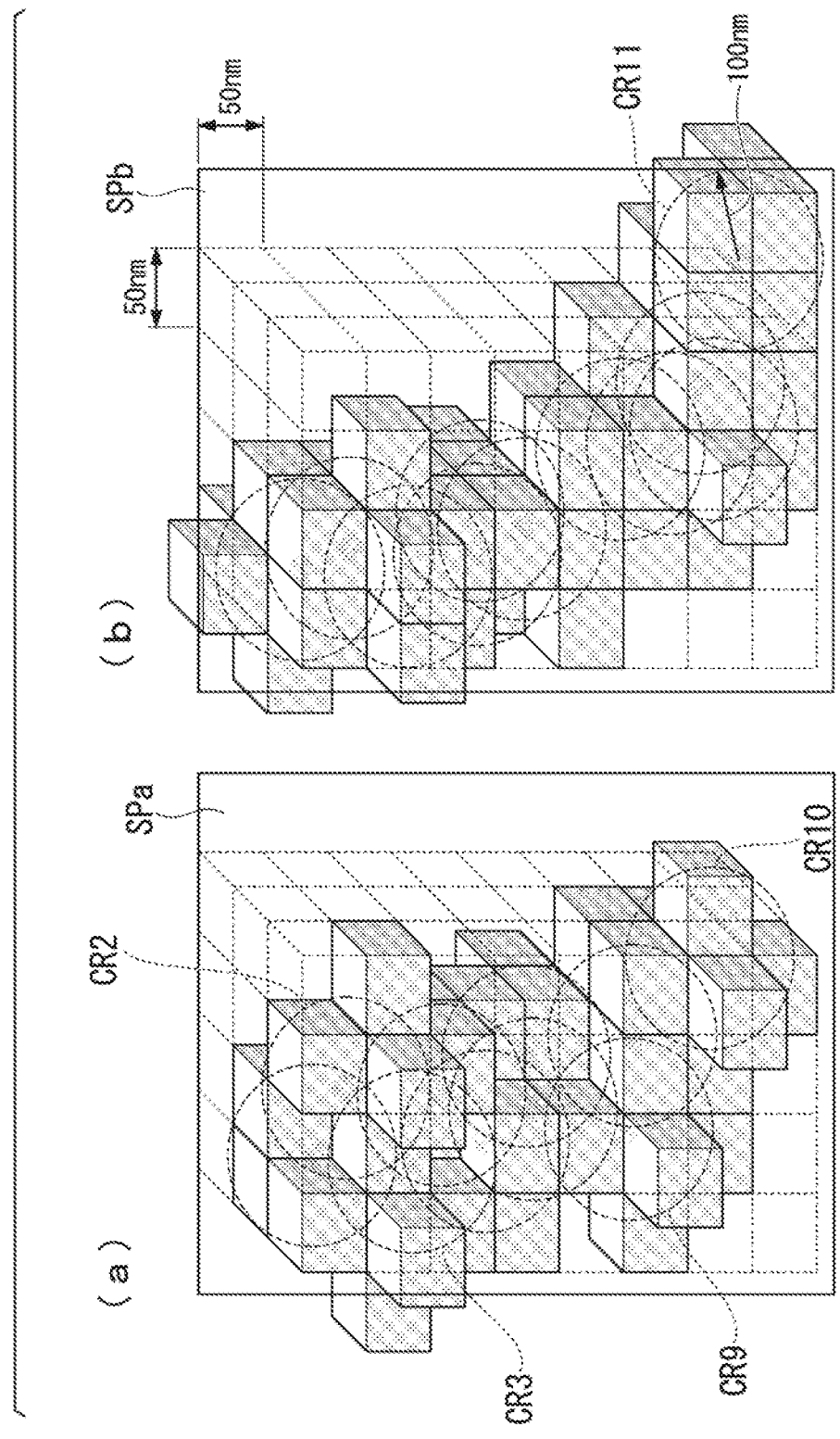
FIG. 11 is a drawing illustrating a method of setting areas corresponding to bright spots in a STORM image in a fourth embodiment.

FIG. 11 is a drawing illustrating a method of setting areas corresponding to bright spots in a STORM image in the present embodiment.

In the present embodiment, a sample picture image is analyzed in accordance with the rules described below as setting method 4.

(Setting Method 4: Case where a Determination Area (Sphere) and Predetermined Areas (Cubes) are Defined, and the Values of the Predetermined Areas are Set to a Value Based on Results Determined by the Determination Area (Sphere).

In the present embodiment, a case is described where a predetermined value is allocated to each of the predetermined areas.

Rule 1: First, the analysis target range is divided into areas based on a grid having preset intervals. Areas shown as divided unit cells are defined as the predetermined areas, each of which constituting an analysis unit.

Note that by forming a grid along orthogonal coordinates, and making the intervals of the grid equal, the predetermined areas, shown as unit cells, will become cubes. For example, when analyzing a sample picture image (three-dimensional image) in real-time in which the presence of two types of molecules varies from moment to moment, the unit cells described above are configured to be cubes, a size thereof defined by a length of one edge being 50 nm.

Rule 2: Next, the determination areas (spheres) corresponding to each bright spot are specified. The radius of the determination areas is set so that the determination areas have a size which is greater than the size of the unit cells (cubes).

Referencing the size of the unit cells described above (cubes, where the length of one side is 50 nm), the size of the determination areas may, for example, set so that the diameter thereof is 200 nm (radius: 100 nm). Because the size of the unit cell and the size of the determination area are set individually, the size of the unit cell and the size of the determination area can easily be set. For example, by setting a sphere with a radius in accordance with the number of photons as the determination area, even if a case arises where the size of the unit cell becomes greater than the size of the sphere, the analysis processing described below can be carried out without the need to adjust the size of the determination area.

Rule 3: Next, a value based on information showing the state of the bright spot positioned at the center of each of the determination areas (spheres) is allocated to each of the determination areas (each sphere). For example, a value proportional to the number of photons of the bright spot may be associated with the information showing the state of the bright spot.

Rule 4: Next, the value in accordance with the determination area (sphere) contained in each of the unit cells (cubes) is set as the value showing the state of the bright spot contained in the unit cell. For example, the number of photons dependent on a ratio of the volume of the determination area (sphere) contained in the unit cell (cube) to the volume of the determination area (sphere) may be set as a constant value in the cube as the value in accordance with the determination area (sphere) contained in the unit cell (cube).

Rule 5: Next, in cases where the areas constituting the plurality of determination areas (spheres) have a portion where the determination areas (spheres) overlap, the sum of the numerical values allocated to each of the overlapping determination areas (spheres) in Rule 4 is calculated, and the resulting sum is set as the value showing the state of the bright spot contained in the unit cell (cube).

Note that in FIG. 11, results through Rule 4 are shown as oblique drawings, and the results of Rule 5 are omitted.

By carrying out processing in accordance with this rule, space can be processed as a unit cell (cube) of desired size. Desired resolution information can be acquired by dividing space into smaller pieces. Additionally, when analyzing sample picture images (data) having different spectra (wavelengths), by using the unit cell (cube) described above, positions in space can be standardized and, as a result, analysis is facilitated. Note that in the present embodiment, the determination areas (spheres) and the predetermined areas (cubes) are set individually, but a configuration is possible wherein only predetermined areas of any cubic shape are set and the numerical value in accordance with the number of bright spots contained in each predetermined area is set as the value that represents the state of the bright spots contained in the predetermined area.

Fifth Embodiment

An aspect of the present embodiment, in which areas corresponding to bright spots are set based on positions of the bright spots in a STORM image, will be described while referencing FIG. 12.

Figure 12:
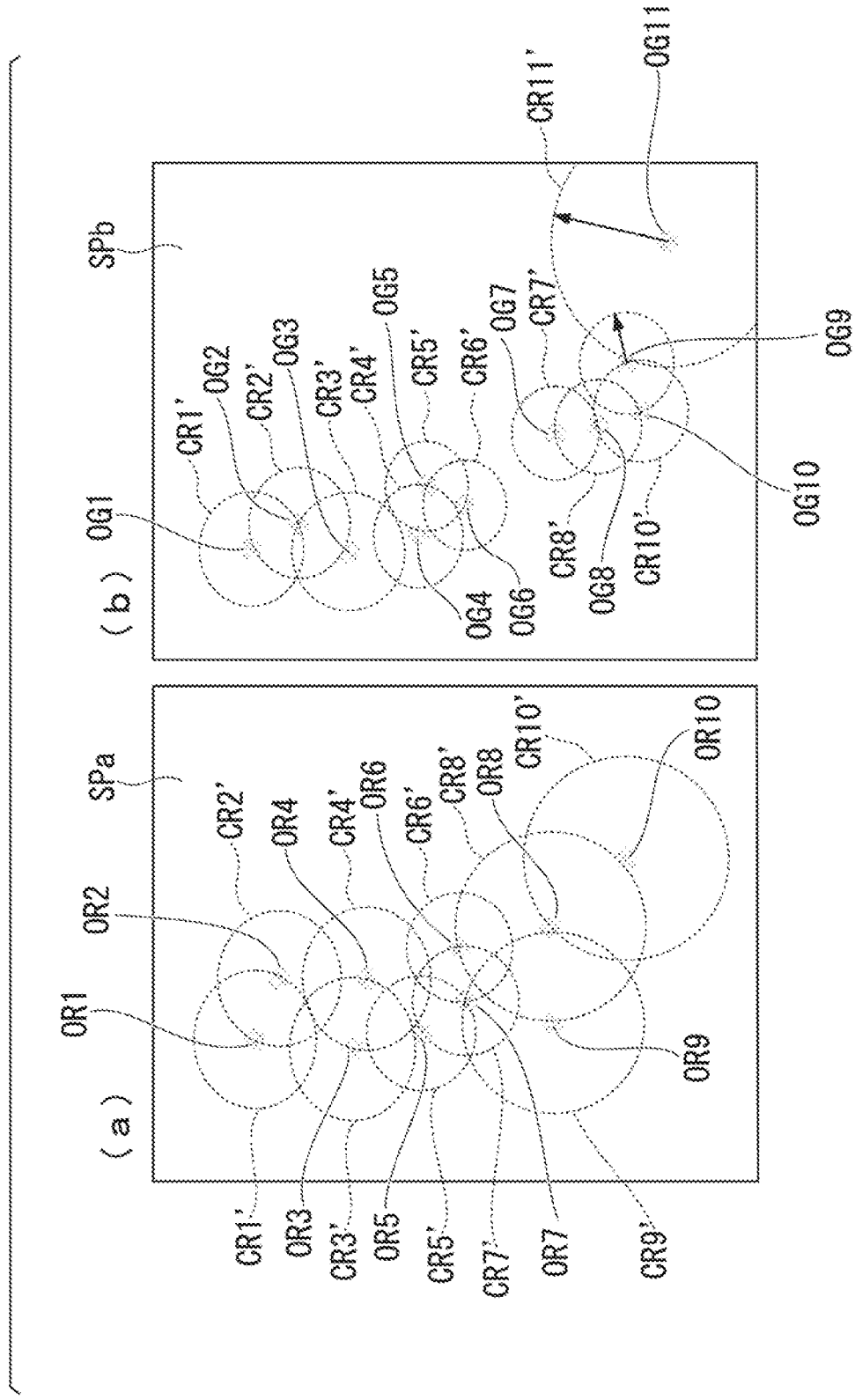
FIG. 12 is a drawing illustrating a method of setting areas corresponding to bright spots in a STORM image in a fifth embodiment.

FIG. 12 is a drawing illustrating a method of setting areas corresponding to bright spots in a STORM image in the present embodiment.

In the present embodiment, a sample picture image is analyzed in accordance with the rules described below as setting method 5.

(Setting Method 5: Case where the Size of the Predetermined Areas is Determined According to the Density of the Bright Spots, and the Predetermined Areas are Filled in with Predetermined Values (Spheres Uniformly Filled in) in Accordance with Information Representing the States of the Bright Spots)

In the present embodiment, a case is described where a predetermined value is allocated to each of the predetermined areas.

The case of the present embodiment differs from the case illustrated in part (a) of FIG. 7 where the spheres CR1 to CR10 have uniform radii. In part (a) of FIG. 12 of the present embodiment, spheres CR1' to CR10' are shown which have radii that differ based on the positions of the bright spots OR1 to OR10. Part (b) of FIG. 12 differs from the case illustrated in part (b) of FIG. 7 where the spheres CG1 to CG11 have uniform radii. In part (b) of FIG. 12 of the present embodiment, spheres CG1' to CG11' are shown which have radii that differ based on the positions of the bright spots OG1 to OG11. The spheres are generated in accordance with the following rules.

Rule 1: First, a sphere is detected having, as its radius, a distance from a first bright spot (reference) to an adjacent second bright spot (closest to the first bright spot). The detected sphere is set as a predetermined area corresponding to the first bright spot. A value representing the state of the bright spot is set in advance for the single bright spot associated with each predetermined area (sphere). For example, a numerical value proportional to the number of photons of the bright spot may be set as the value representing the state of the bright spot.

Rule 2: Values calculated from the value representing the state of each of the bright spots and the volume of the predetermined areas (spheres) are allocated to each of the areas in the spheres shown as predetermined areas. For example, the result of dividing the value based on the information showing the state of the first bright spot by the value showing the size (volume) occupied by a first area may be set as the value representing the state of the bright spot contained in the first area.

Note that in cases where there is a plurality of predetermined areas (spheres) and the predetermined areas (spheres) have an overlapping portion, the sum of the numerical values allocated to each of the overlapping predetermined areas (spheres) in Rule 2 may be calculated, and the resulting sum may be newly allocated as the value of the overlapping area of the predetermined areas (spheres).

Following the rules described above, the size of each of the predetermined areas is set according to the density of the bright spots that are present therein, and the number of photons of the bright spots can be distributed in accordance with said density. In other words, the value allocated to each region can be made to vary in accordance with the density at which the bright spots are present.

By carrying out processing in accordance with these rules, a predetermined area (sphere), of a size set in accordance with the density at which the bright spots are present, can be set and processing carried out. Resolution can be increased in cases where the density at which the bright spots are present is high, and resolution can be decreased in cases where the density at which the bright spots are present is low. As described above, resolution can be adjusted on the basis of the density at which the bright spots are present and, as a result, the calculation processing load can be adjusted according to the density at which the bright spots are present and analyses can be efficiently carried out.

As shown in the embodiments, the microscope device 10 (analysis device) can perform quantitative analysis based on images of high resolution.

Although only a few embodiments of the present invention have been described, it should be understood that the present invention may be embodied in many other specific forms without departing from the spirit or the scope of the present invention.

For example, in the embodiments, cases are described where STORM is given as the type of fluorescent microscope device used to acquire images of super resolution and quantitative analyses based on images acquired using these methods are carried out. However, the present invention also can be applied to cases where quantitative analysis is carried out on images (sample picture images) captured using photoactivation localization microscopy (PALM) technology such as that described in U.S. Pat. No. 7,626,695 and the like.

An example of the fluorescent material used when employing PALM is Dronpa. Dronpa has properties whereby when irradiated with light of a given intensity, Dronpa is enabled to absorb the excitation wavelength. Additionally, Dronpa does not emit fluorescence while in an inactive state, even when irradiated with excitation light. Accordingly, just as in STORM, low-resolution fluorescent images and high-resolution fluorescent images can be acquired by adjusting the intensity of light radiated on the sample. By using the low-resolution fluorescent images as mask images, quantitative analysis can be carried out on the high-resolution images.

Alternatively, the present invention also can be applied to cases where quantitative analysis is carried out on images (sample picture images) captured using stimulated emission depletion (STED) microscopy, in which images are observed by irradiating the optical system of a galvanometer mirror-based confocal microscope with two types of laser light—excitation laser light for observation and short pulse laser light for inducing emission—nearly simultaneously. In this case as well, images according to the embodiments of the present invention or images acquired via structured illumination microscopy (SIM) as described above can be used as a conventional image. Note that various aspects of the embodiments described above may be combined as appropriate. Moreover, some of the component parts may be removed. Moreover, to the extent permissible by law, all publications and US patent documents related to the devices or the like used in the embodiments and modification examples as described above are incorporated herein by reference.

REFERENCE SIGNS LIST

10 Microscope device (analysis device)
11 Excitation illumination system
13 Activation illumination system
14 Control unit
15 Microscope main body
16 Storage unit
17 Display unit
21, 42 Laser light source
22 Shutter
31 Stage
32 Total reflection mirror
33 Dichroic mirror
34 Camera
43 Scanner
61 Mercury lamp
141 Initialization processing unit
142 Picture image forming unit
143 Sample picture image analysis unit
L1 Excitation light
L2 Activation light
S101 Initialization process step
S102 Sample picture image generation step
S103 Sample picture image analysis step
G1 Conventional image
G2 STORM image

What is claimed is:

1. A device comprising:
a processor programmed to:
specify, in a fluorescent image, at least a first region and a second region in an analysis target range, and calculate region quantitative information of the first region based on information regarding a bright spot included in the first region;
calculate region quantitative information of the second region based on information regarding a bright spot included in the second region; and calculate region quantitative information of an overlapping region in which the first and second regions overlap based on the region quantitative information of the first region and the region quantitative information of the second region, whereby quantitative analysis on the fluorescent image, which is a sample picture image of high resolution, is performed by the processor.

2. The device according to claim 1, wherein the first and second regions are specified based on positions of the bright spots.

3. The device according to claim 1, wherein the first region or the second region is a circle or a sphere.

4. The device according to claim 1, wherein the processor is programmed to calculate the region quantitative information of the overlapping region using a sum of the region quantitative information of the first region and the region quantitative information of the second region.

5. The device according to claim 1, wherein the processor is programmed to
   calculate the region quantitative information of the first region using the information regarding the bright spot included in the first region and information regarding a size of the first region, and
   calculate the region quantitative information of the second region using the information regarding the bright spot included in the second region and information regarding a size of the second region.

6. The device according to claim 1, wherein the information regarding the bright spots included in the first and second regions is information regarding a number of the bright spots.

7. The device according to claim 1, wherein the information regarding the bright spots included in the first and second regions is information regarding a number of photons of the bright spots.

8. A system comprising:
the device of claim 1;
an optical system by which a sample including fluorescent material is irradiated with activation light and excitation light;
a camera by which an image of the fluorescent material is captured; and
an image generator by which the fluorescent image is generated based on position information of the image of the fluorescent material.

9. A method using a processor, the method comprising:
specifying, in a fluorescent image, at least a first region and a second region in an analysis target range, and calculating region quantitative information of the first region based on information regarding a bright spot included in the first region;
calculating region quantitative information of the second region based on information regarding a bright spot included in the second region; and
calculating region quantitative information of an overlapping region in which the first and second regions overlap based on the region quantitative information of the first region and the region quantitative information of the second region, whereby quantitative analysis on the fluorescent image, which is a sample picture image of high resolution, is performed by the processor.

10. A non-transitory computer readable medium storing a program causing a processor of a computer to execute steps of:
specifying, in a fluorescent image, at least a first region and a second region in an analysis target range, and calculating region quantitative information of the first region based on information regarding a bright spot included in the first region;
calculating region quantitative information of the second region based on information regarding a bright spot included in the second region; and
calculating region quantitative information of an overlapping region in which the first and second regions overlap based on the region quantitative information of the first region and the region quantitative information of the second region, whereby quantitative analysis on the fluorescent image, which is a sample picture image of high resolution, is performed by the processor.

\* \* \* \* \*